Figure 1:
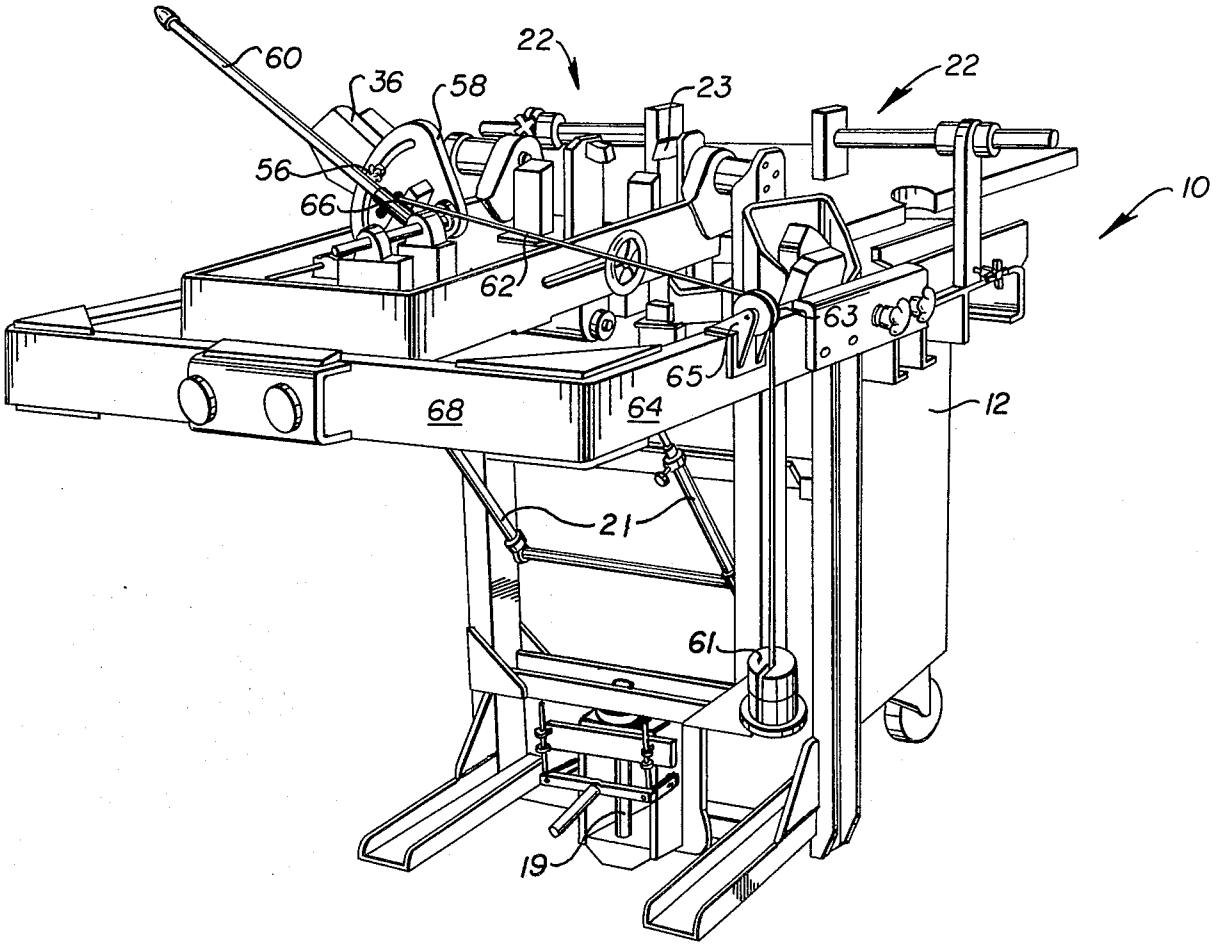
Figure 2:
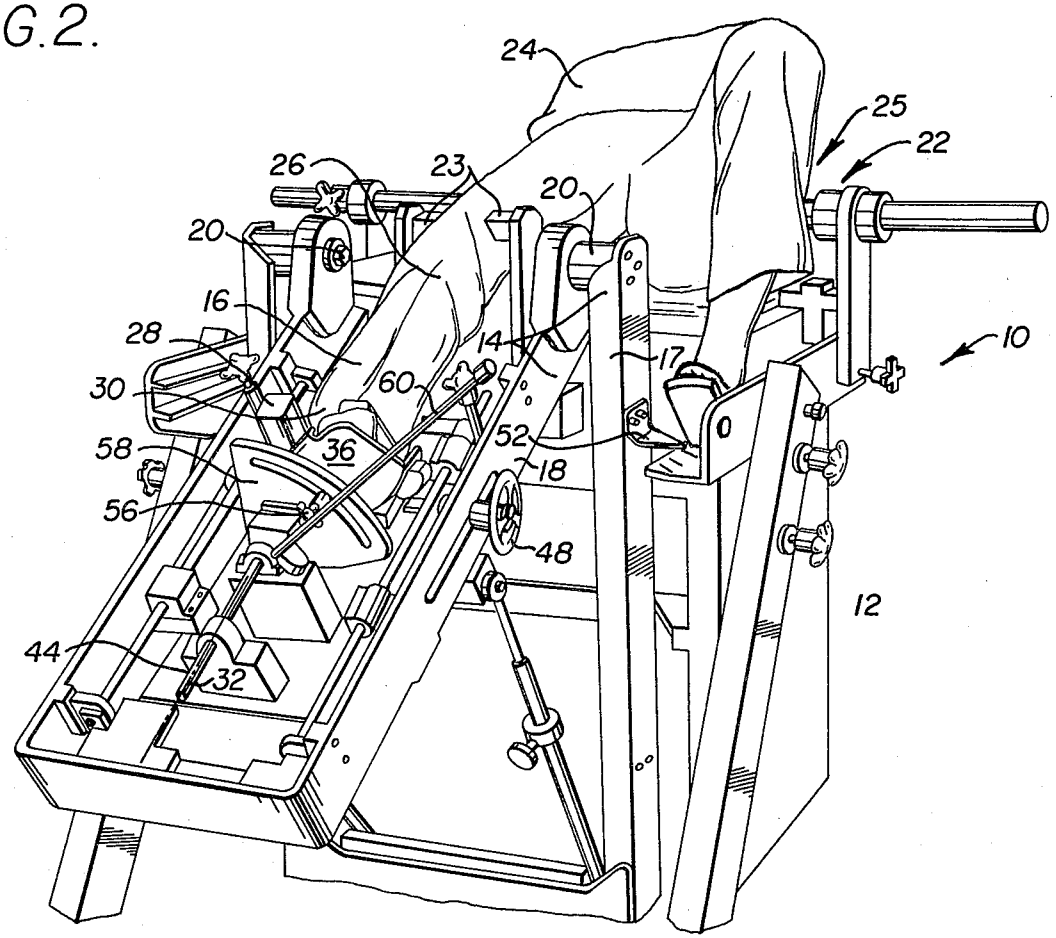
Figure 3:
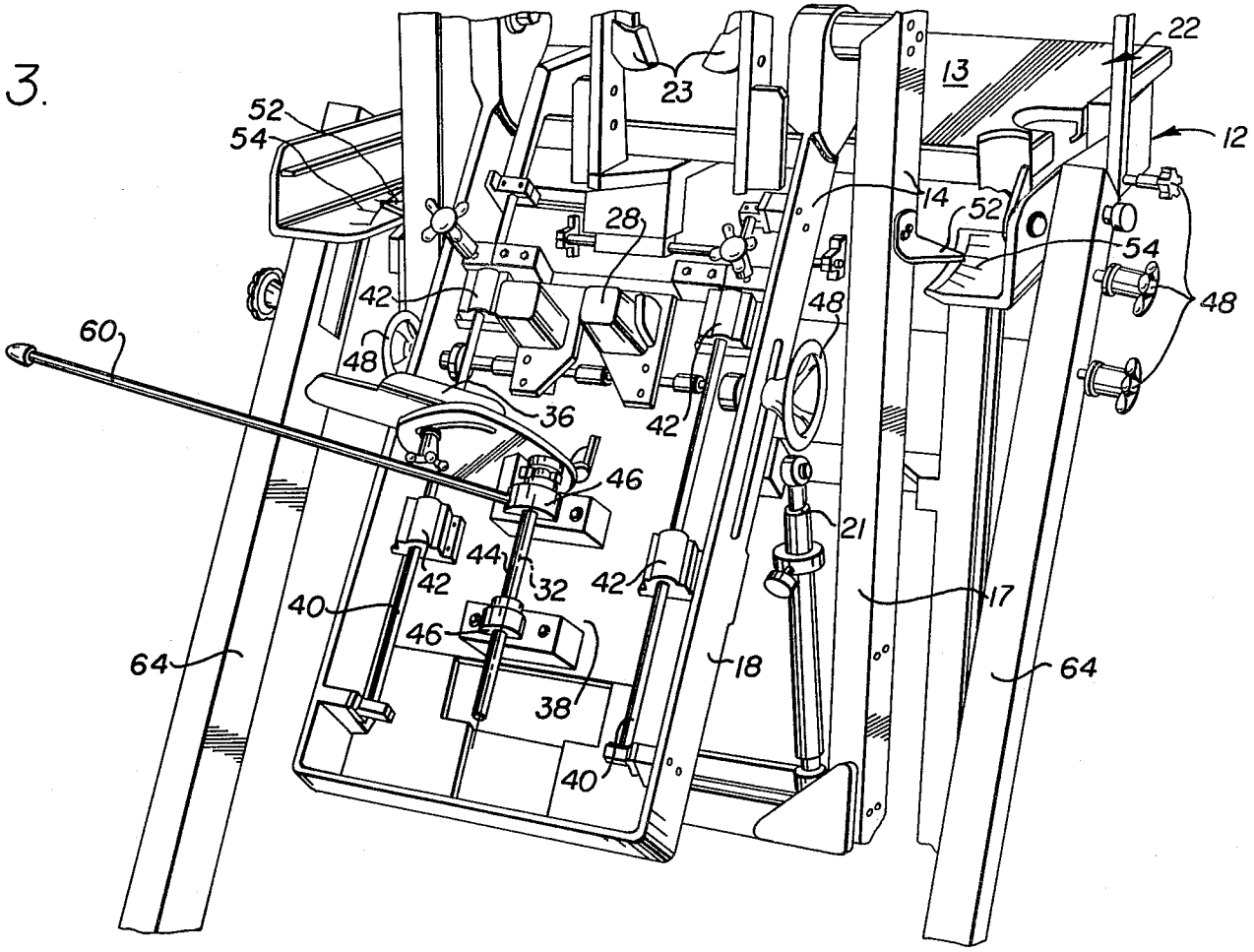
Figure 4:
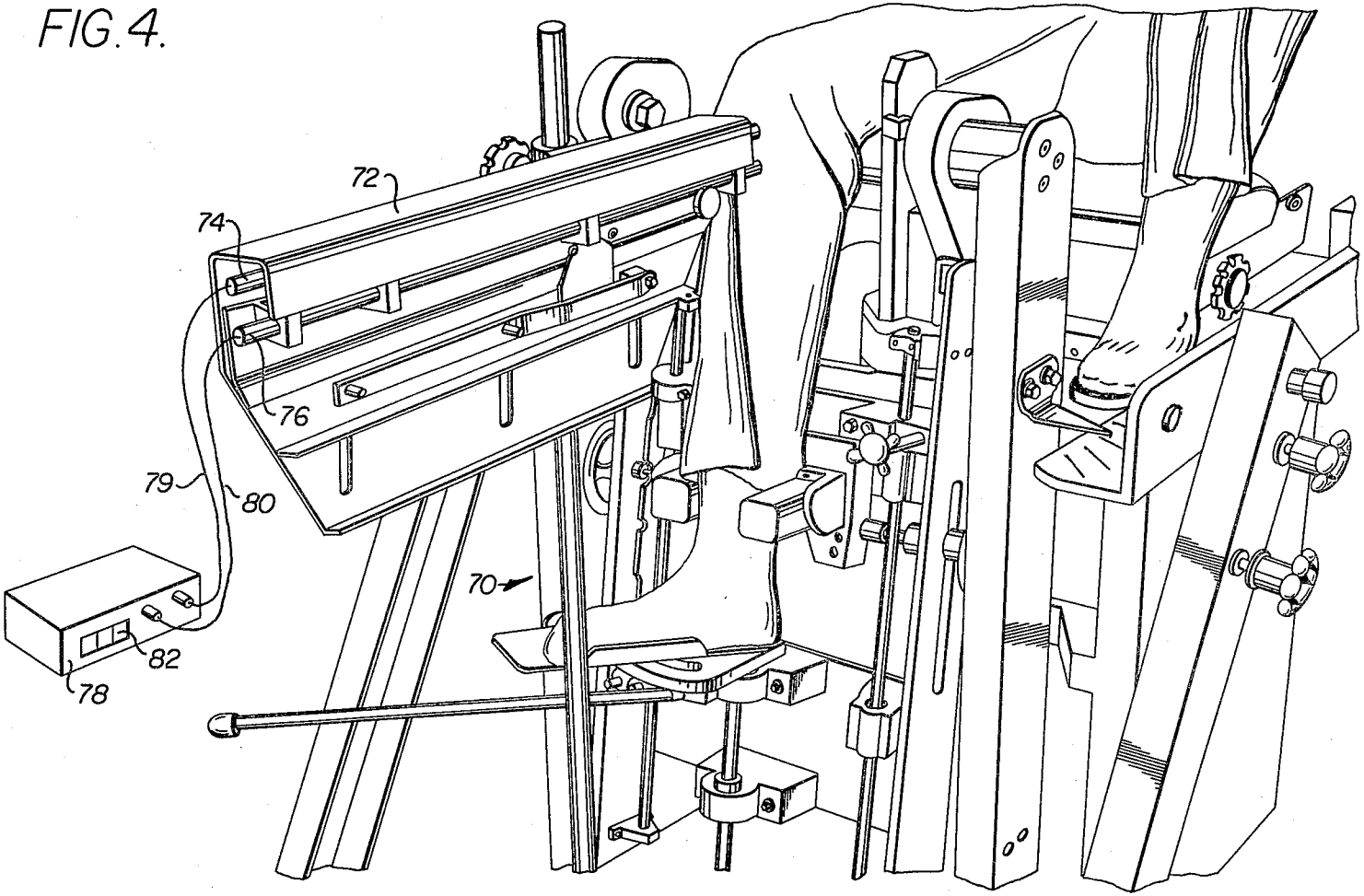

United States Defensive Publication [19] (H) [11] T100,602

Roley et al. [43] May 5, 1981

[54] APPARATUS FOR MEASURING ANGLES

[76] Inventors: Daniel G. Roley, R.R. #3, Box V-78, Chillicothe, Ill. 61523; Paul L. Wright, 4321 Nelson Dr., Peoria, Ill. 61614

[21] Appl. No.: 86,985

[22] Filed: Oct. 22, 1979

[51] Int. Cl.[3] ..... A61B 5/10

[52] U.S. Cl. ..... 128/782; 33/174 P

[57] ABSTRACT

An apparatus for measuring angles of displacement between human femur and tibia leg bones to determine the stability (stiffness and laxity) of a knee joint has structure and instruments for checking upper and lower leg bone alignment, angulation and degree of relative lateral displacement. A platform is provided to support and secure a human torso about its hips while auxiliary inner and outer coacting frame support structure adjustably secures the leg bones. Sensing and indicating instruments associated with the coacting frame structure and an auxiliary detachable support frame contact the leg and foot to give a reading on leg and knee stability as the lower leg bone (tibia) and the foot are selectively placed at various angles while predetermined side loads on the tibia are simultaneously applied.

1 Claim, 4 Sheets Drawing,

9 Pages Specification

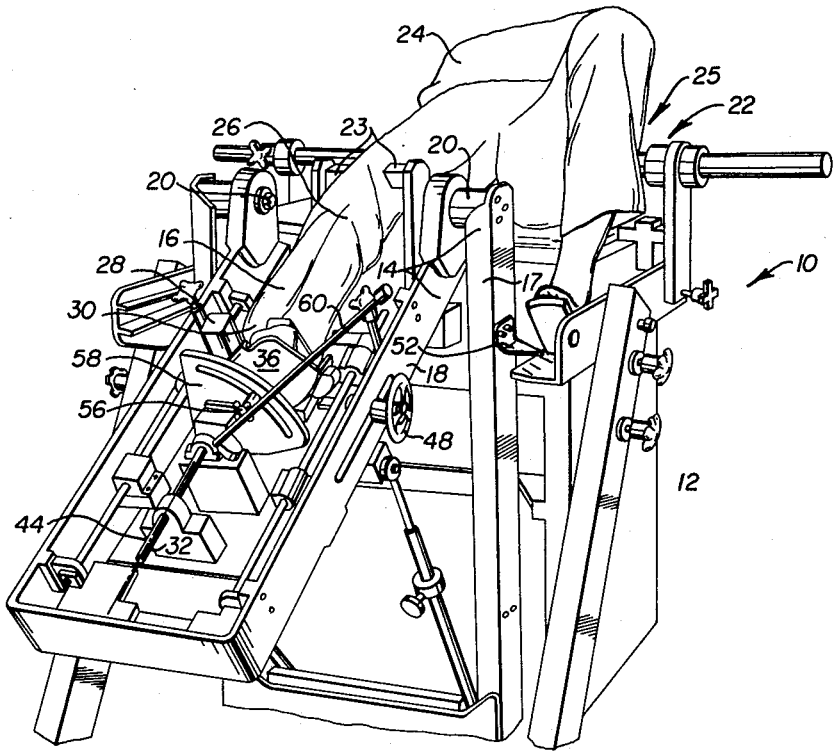

The file of this unexamined application may be inspected and copies thereof may be purchased (849 O.G. 1221, Apr. 9, 1968).